United States Patent
Miller

(10) Patent No.: US 7,757,303 B2
(45) Date of Patent: Jul. 20, 2010

(54) FORELIMB BRACE DEVICE

(76) Inventor: James R. Miller, 40 Parkwood Dr., Milton, MA (US) 02186

(*) Notice: Subject to any disclaimer, the term of this patent is extended or adjusted under 35 U.S.C. 154(b) by 1286 days.

(21) Appl. No.: 10/501,639

(22) PCT Filed: Jan. 16, 2003

(86) PCT No.: PCT/US03/01477

§ 371 (c)(1), (2), (4) Date: Apr. 13, 2005

(87) PCT Pub. No.: WO03/061411

PCT Pub. Date: Jul. 31, 2003

(65) Prior Publication Data

US 2005/0172973 A1 Aug. 11, 2005

Related U.S. Application Data

(60) Provisional application No. 60/349,102, filed on Jan. 16, 2002.

(51) Int. Cl. *A41D 13/00* (2006.01)
(52) U.S. Cl. ................. 2/16; 128/878; 602/62
(58) Field of Classification Search ......... 2/16, 2/20, 21, 22, 159, 160, 161.1, 162; 128/877, 128/878, 879; 602/5, 20–22, 62, 64
See application file for complete search history.

(56) References Cited

U.S. PATENT DOCUMENTS

| | | | |
|---|---|---|---|
| 5,313,667 A | 5/1994 | Levine | |
| 5,375,263 A * | 12/1994 | Cuccia | 2/158 |
| 5,383,844 A * | 1/1995 | Munoz et al. | 602/20 |
| 5,383,845 A | 1/1995 | Nebolon | |
| 5,537,692 A | 7/1996 | Dorr | |
| 5,722,092 A | 3/1998 | Borzecki et al. | |
| 5,870,773 A | 2/1999 | Smith | |
| 5,898,936 A | 5/1999 | Janes | |
| 5,953,752 A | 9/1999 | Jones | |
| 6,721,959 B1 * | 4/2004 | Hairston | 2/16 |

FOREIGN PATENT DOCUMENTS

| JP | 10248863 A | 9/1998 |
|---|---|---|
| WO | WO98/17132 | 4/1998 |

* cited by examiner

*Primary Examiner*—Tejash Patel
(74) *Attorney, Agent, or Firm*—Hamilton, Brook, Smith & Reynolds, P.C.

(57) ABSTRACT

A forelimb brace device suitable for use by snowboarders, skiers, in-line skaters and others protects against hyperextension and other injuries, by maintaining a selected orientation of the fingers, hand, wrist and forearm within a substantially rigid shell assembly having a palmar arch grip element and tensioning elements for maintaining a selected tension of the palmer element across the users' hand and forearm. The forelimb is maintained in a flexed position, while an extension stop prevents hyperextension of the phalanges, and a thumb portion prevents abduction or opposition injuries to the thumb.

14 Claims, 6 Drawing Sheets

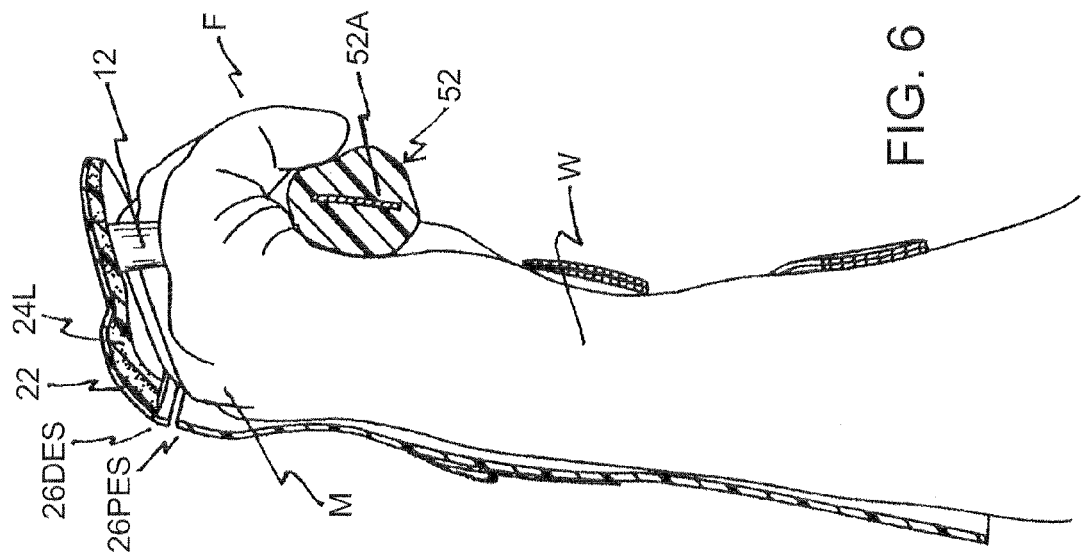
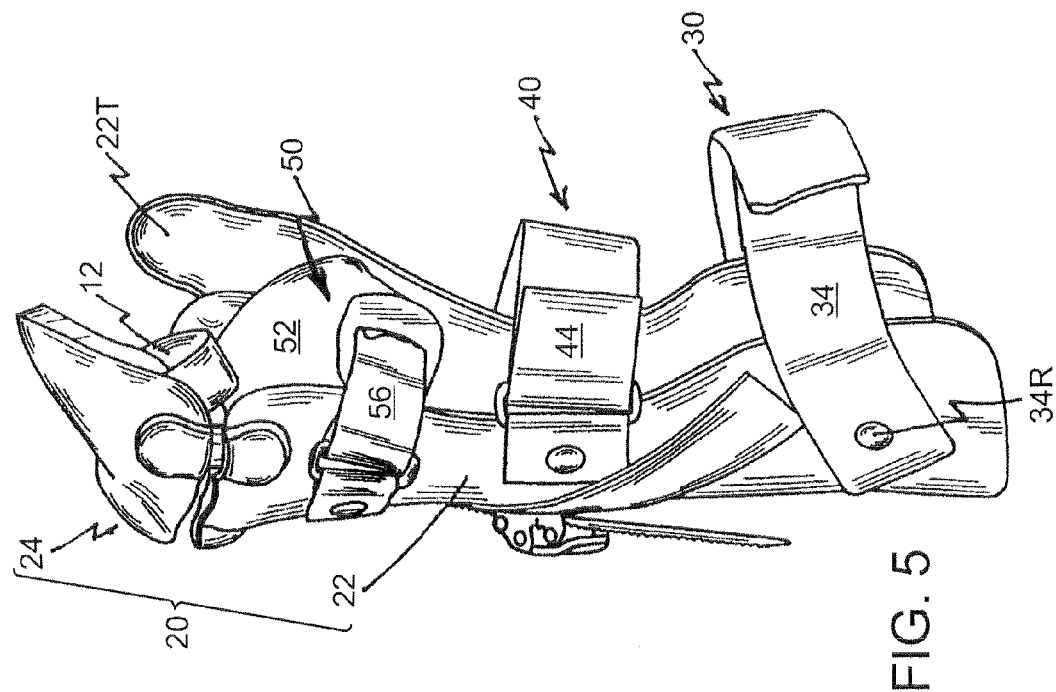

FORELIMB BRACE DEVICE

CROSS-REFERENCE TO RELATED APPLICATIONS

This application is based upon and claims priority from U.S. provisional patent application Ser. No. 60/349,102, filed 16 Jan. 2002, entitled FORELIMB BRACE.

FIELD OF THE INVENTION

The invention relates generally to devices and methods for protecting bones and joints of the human anatomy, and in particular, to a forelimb brace device configured to protect the hand, wrist, and forearm from injuries during snowboarding, skateboarding, skating, and other such activities.

BACKGROUND OF THE INVENTION

With the explosion of the popularity of snowboarding and other activities such as skateboarding and in-line skating have come serious injuries such as wrist sprains and fractures. Such injuries are typically the result of participant using his/her arm(s) to cushion a fall during such activities, which generally results in a high-energy impact of the involved hand, wrist, and forearm with an immovable mass such as the ground or a sidewalk. Such high-energy impacts quite often result in muscle sprains, bone fractures, and hyperextensions.

Wrist and other types of braces are known in the art for protecting the hand, wrist, and/or forearm during such high-energy impacts. Examples of such braces are shown in the representative U.S. and international patents listed below, which are incorporated herein by reference:
U.S. Pat. No. 5,313,667
U.S. Pat. No. 5,537,692
U.S. Pat. No. 5,722,092
U.S. Pat. No. 5,870,773
U.S. Pat. No. 5,898,936
U.S. Pat. No. 5,593,752
WO 98/17132
JP 102 48863A However, the braces disclosed in these patents suffer from limitations and deficiencies. For example, some are cumbersome to use, and many fail to provide sufficient protection against injuries such as "Gamekeeper's Thumb" (hyperextension) and finger or wrist sprains and fractures which can include, for example, hyperextension of the wrist. Novice snowboarders, skateboarders, skaters and participants in other such activities frequently injure themselves by falling backwards or sideways and attempting to break such falls with their hands extended, e.g., hyperextending their wrists.

Accordingly, it is desirable to provide a forelimb brace assembly that is simple to use and provides enhanced protection against injuries to the hand, wrist, and/or forearm such as the Gamekeeper's Thumb, finger injuries, and wrist injuries during snowboarding, skateboarding, skating, and other such activities.

SUMMARY OF THE INVENTION

An adjustable hand, wrist and forearm brace device suitable for use by snowboarders, skateboarders, skiers, in-line skaters and participants in other such activities protects against hyperextension and other lower arm injuries, by maintaining a selected orientation of the fingers, hand, wrist and forearm within a substantially rigid shell assembly having a palmar arch grip element and tensioning elements for maintaining a selected tension of the palmar element across the users' hand and forearm. The hand and wrist are maintained in a flexed position, while an extension stop prevents hyperextension of the metacarpophalangeal (MCP) joint and phalanges, and a thumb portion prevents abduction or other injuries to the thumb.

BRIEF DESCRIPTION OF THE DRAWINGS

The accompanying drawings, which are hereby incorporated into and constitute a part of this specification, illustrate embodiments of the invention. When considered with the description set forth herein, the drawings serve to explain the principles of the invention by way of example, but without limitation as to the scope of the invention, which is defined by the claims appended hereto. In the drawings, like reference numerals are used to represent like parts throughout the various views, and the following descriptions apply:

FIG. 5 is a lateral, side view of the forelimb brace device of FIG. 2 showing the proximal support shell, the thumb portion of the proximal support shell, the distal support shell, a finger anchor strap, the palmar arch grip, palmar grip anchor straps, an adjustable, ratchet style strap assembly, wrist anchor members, forearm anchor members, strap elements, and metacarpophalangeal joint mechanisms of this embodiment of the invention.

FIG. 6 is a cut away, side sectional, lateral view of the forelimb brace device of FIG. 2 showing the forearm section with the interconnected wrist section and a hand section resting in the forelimb brace, the said hand section engaging the palmar arch grip of this embodiment of the invention.

DETAILED DESCRIPTION OF THE INVENTION

Figure 1:
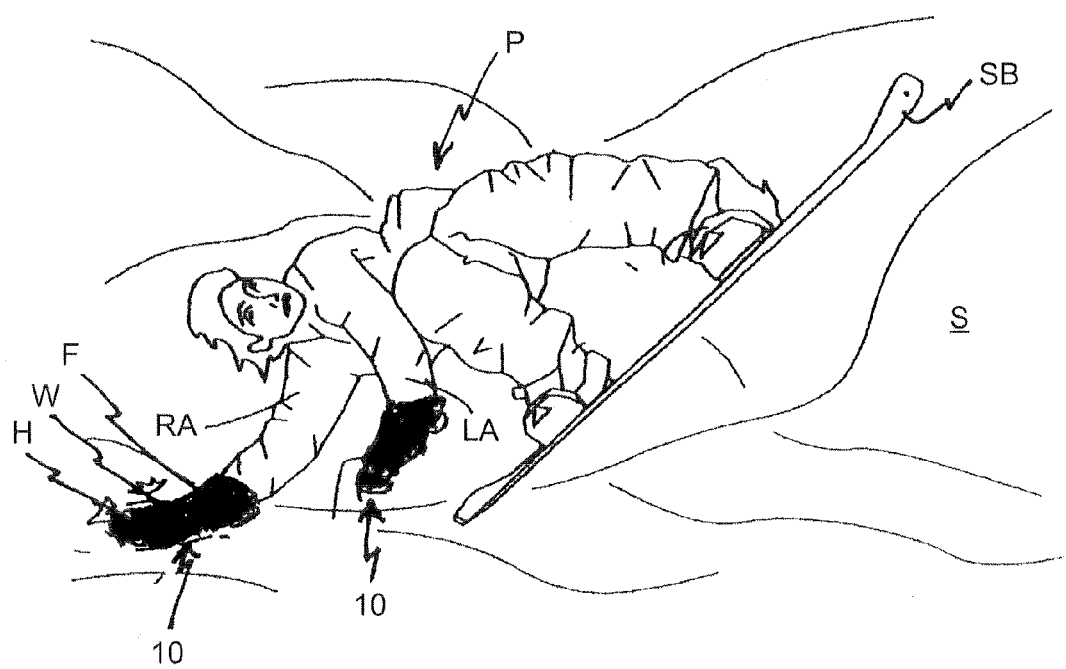
FIG. 1 is a perspective view of a snowboard rider in an act of falling predominately on his/her right lower arm which is protected by being enclosed by a forelimb brace device according to the present invention.

Referring now to the drawings wherein like reference numerals identify corresponding or similar elements throughout the several views, FIG. 1 illustrates a forelimb brace device 10 according to the present invention for use by snowboarders, skateboarders, skiers, inline skaters and other such activities where there is an appreciable risk that participants in such activities will be subjected to one or more lower arm, i.e., finger, hand, wrist and/or forearm, injuries. The forelimb brace device 10 is configured to provide enhanced protection to the lower arm, thereby effectively eliminating injuries thereto. In addition to its protective function, the forelimb brace device 10 of the present invention also has utility as a stabilizing structure, e.g., "outrigger", for snowboarders and skateboarders. A snowboarder for example, can use the forelimb brace device 10 as a structural support against snow or ice to maintain his/her balance or position in toe-side turns.

As shown in the example of FIG. 1, a participant P is wearing the forelimb brace device 10 while riding on a snowboard SB over a surface S. The participant P is shown in the act of falling, with his/her right and left arms RA, LA extended outwardly to cushion the participant P against such fall. The participant P is using the forearm F, wrist W and hand H of his/her extended right arm RA as a brace against the surface S—as a snowboarder might do in a typical fall. In falls of this type, snowboarders frequently suffer lower forearm injuries such as hyperextended wrists and/or fingers and/or fractures of the bones of the fingers, hand, wrist or forearm.

Brace Details

FIGS. 2 through 8 illustrate one embodiment a forelimb brace device 10 according to the present invention. This embodiment of the forelimb brace device 10 includes a protective shell assembly 20, an adjustable forearm anchoring mechanism 30, an adjustable wrist anchoring mechanism 40, an adjustable palmar-grip anchoring mechanism 50, and a finger retention strap 12.

The protective shell assembly 20 includes a proximal support shell 22, a distal support shell 24, and a metacarpophalangeal (MCP) joint subassembly 26. The proximal support shell 22 includes a thumb extension 22T as shown. Support shells 22, 24 are fabricated using know fabrication techniques, e.g., molding, as rigid structures, preferably from a substantially rigid thermoplastic or other suitable stiff or semi-rigid material such as high density polyethylene (HDPE) or the like. The support shells 22, 24 are fabricated with a thickness sufficient to provide protection against the forces that the forelimb brace device 10 may be subjected to during high-energy impacts with a surface.

The proximal support shell 22 is fabricated in a configuration wherein the shell 22 conforms to and overlays the dorsal surfaces of the forearm and the hand (including the thumb) and all or substantially all of the ulnar and radial surfaces of the forearm and the hand. The distal support shell 24 is fabricated in a configuration wherein the shell 24 conforms to and overlays the fingers in a curled position (see discussion below in connection with the palmar-grip anchoring mechanism 50). The support shells 22, 24 can be fabricated in standard sizes, e.g., small, medium, and large, for men, women, and children, or can be custom fabricated for any particular individual.

Optionally, depending upon the circumstances in which the forelimb brace device 10 is used, the distal support shell 24 includes inner support layer 24SL of a relatively soft, compressible foam material such as polyurethane or a similar material as best illustrated in FIG. 6 (the embodiment of the forelimb brace device 10 illustrated in FIGS. 2-8 includes only the inner support layer 24L). Alternatively, the proximal support shell 22 can include an inner support layer (not illustrated) wherein the inner support layer of the proximal support shell 22 and the inner support layer 24SL in combination define a shell inner liner for the protective shell assembly 20. The inner support layers are affixed to the support shells 22, 24, respectively, by any conventional means, e.g., adhesive, rivets, bonding, etc. The inner support layers, where incorporated in the forelimb brace device 10, prevent chafing of the skin against the inner surfaces of the proximal support shell 22 and/or the distal support shell 24 and provide a force-absorbing capability where the forelimb brace device 10 is secured directly against the skin of a user (or where only a thin-layered garment covers the forearm of the user). When the forelimb brace device 10 is used in conjunction with cold weather activities, where the user is typically wearing thick, i.e., well cushioned, upper body clothing and/or gloves wherein such clothing and/or gloves provide the anti-chafing and force-absorbing capabilities of the inner support layers, which may be completely or partially omitted from the forelimb brace device 10.

Figure 3:
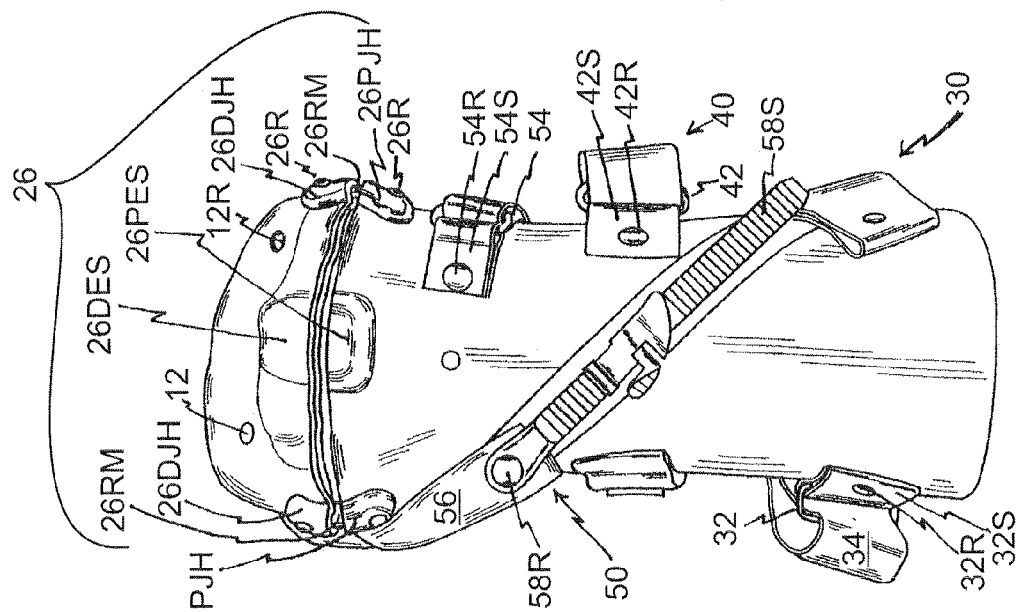
FIG. 3 is a dorsal perspective view of the forelimb brace device of FIG. 2, showing the proximal support shell, the thumb portion of the proximal support shell, the distal support shell, a finger anchor strap, palmar grip anchor straps, an adjustable, ratchet style strap assembly, wrist anchor members, forearm anchor members, strap elements, and metacarpophalangeal joint mechanisms of this embodiment of the invention.

The MCP joint assembly 26 is configured to integrate the distal support shell 24 in combination with the proximal support shell 22 in such as manner that the distal support shell 24 is capable of limited movement (pivotal) with respect to the proximal support shell 22. The MCP joint assembly 26 includes proximal joint housings 26PJH, corresponding distal joint housings 26DJH, resilient members 26RM, and proximal and distal stop structures 26PES, 26DES. The proximal joint housings 26PJH and the distal joint housings 26DJH are fabricated as integral structures in the proximal support shell 22 and the distal support shell 24, respectively, of the described embodiment of the forelimb brace device 10 (see FIG. 3). One end of each of the resilient members 26RM is affixed in the proximal joint housings 26PJH by any conventional fastening means, preferably rivets 26R as illustrated in FIG. 3 and the other end of the resilient members 26RM is affixed in the distal joint housings 26DJH by any conventional fastening means, preferably rivets 26R as illustrated in FIG. 3. The proximal and distal stop structures 26PES, 26DES are fabricated as integral members of the proximal support shell 22 and the distal support shell 24, respectively (see FIGS. 3, 4).

The adjustable forearm anchoring mechanism 30 and the adjustable wrist anchoring mechanism 40 are operative to anchor or secure the proximal support shell 22 against the forearm and wrist, respectively, of a user. The adjustable forearm anchoring mechanism 30 and the wrist anchoring mechanism 40 are configured to be adjustable in tension so that the anchoring or securing force provided by the adjustable forearm and wrist anchoring mechanisms 30, 40 can be adjusted as required to properly anchor or secure the forelimb brace device 10 to the forearm and wrist of a user. The adjustable forearm and wrist anchoring mechanisms 30, 40 are also configured so that applied tension can be readily relieved to facilitate removal of the forelimb brace device 10 by the user.

The illustrated adjustable forearm anchoring mechanism 30 comprises a retaining ring 32 and a hook and loop fastener (e.g., VELCRO®) anchor strap 34. The retaining ring 32 is attached to one lateral surface (either ulnar or radial) of the proximal support shell 22 adjacent the end thereof distal the thumb extension 22T by any conventional means, e.g., a strap 32S affixed to the radial surface of the proximal support shell 22 by means of a rivet 32R as illustrated in FIG. 3, and one end of the anchor strap 34 is affixed to the other lateral surface (either radial or ulnar) of the proximal support shell 22 in opposed relation to the retaining ring 32 by any conventional means, e.g., a rivet 34R is illustrated in FIG. 5. The free end of the anchor strap 34 is looped through the retaining ring 32 and folded back upon itself so that the free end can be appropriately tensioned and then removably attached to a portion of the strap 34 adjacent the affixed end thereof to securely fit/position the forelimb brace device 10 against the forearm of the user.

One skilled in the art will appreciate that other mechanisms can be used as the adjustable forearm anchoring mechanism to anchor or secure the forearm of the user against the proximal support shell 22. For example, a belt and buckle combination can be used to provide forearm tensioning of the proximal support shell 24. Alternatively, a ratchet assembly of the type described herein (as part of the adjustable palmar-grip anchoring mechanism 50) can be used to provide forearm tensioning of the proximal support shell 24.

Figure 4:
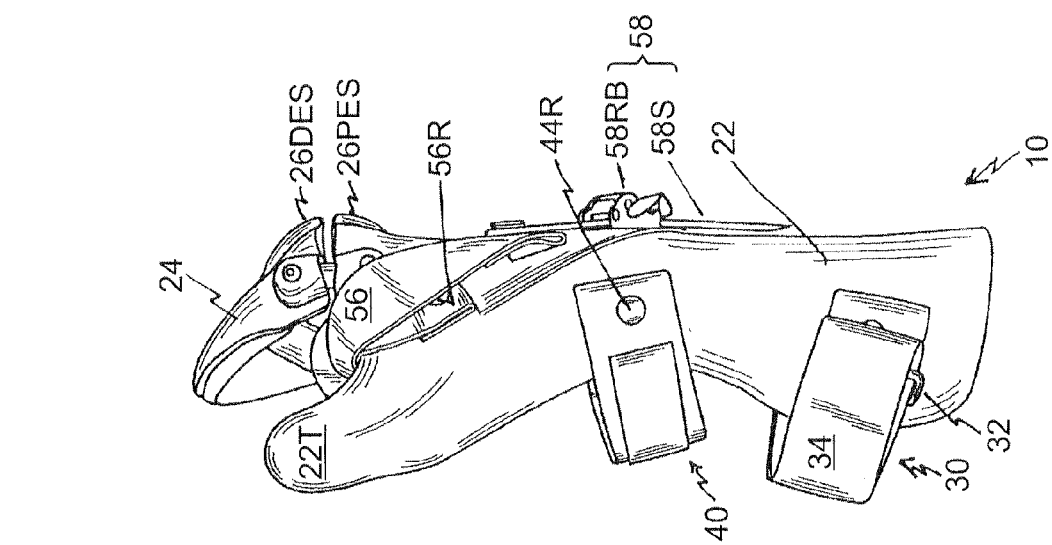
FIG. 4 is a medial, side view of the forelimb brace device of FIG. 2 showing the proximal support shell, the thumb portion of the proximal support shell, the distal support shell, a finger anchor strap, palmar grip anchor straps, an adjustable, ratchet style strap assembly, wrist anchor members, forearm anchor members, strap elements, and metacarpophalangeal joint mechanisms of this embodiment of the invention.

The illustrated adjustable wrist anchoring mechanism 40 is identical to the adjustable forearm anchoring mechanism 30 described in the preceding paragraph and comprises a retaining ring 42 and a hook and loop fastener anchor strap 44. The retaining ring 42 is attached to one lateral surface (either ulnar or radial) of the wrist section of the proximal support shell 22 by any conventional means, e.g., a strap 42S affixed to ulnar surface of the proximal support shell 22 by means of a rivet 42R as illustrated in FIG. 3, and one end of the anchor strap 44 is affixed to the other lateral surface (either radial or ulnar) of the proximal support shell 22 in opposed relation to the retaining ring 42 by any conventional means, e.g., a rivet 44R as illustrated in FIG. 4. The free end of the anchor strap 44 is looped through the retaining ring 42 and folded back upon itself so that the free end can be appropriately tensioned and then removably attached to a portion of the strap 44 adjacent the affixed end thereof to securely fit the forelimb brace device 10 against the wrist of the user.

One skilled in the art will appreciate that other mechanisms can be used as the adjustable wrist anchoring mechanism to anchor or secure the wrist of the user against the proximal support shell 22. For example, a belt and buckle combination can be used to provide wrist tensioning of the proximal support shell 24. Alternatively, a ratchet assembly of the type described herein (as part of the adjustable palmar-grip anchoring mechanism 50) can be used to provide wrist tensioning of the proximal support shell 24.

The embodiment of the adjustable palmar-grip anchoring mechanism 50 illustrated in FIGS. 2-8 comprises a palmar grip 52, a retaining ring 54, a grip strap 56, and a ratchet assembly 58. The retaining ring 54 is attached to the dorsal surface (or alternatively the ulnar surface) of the proximal support shell 22 adjacent the end thereof proximal the distal support shell 24 by any conventional means, a strap 54S affixed to the proximal support shell 22 by means of a rivet 52R as illustrated in FIG. 3.

The palmar grip 52 has an external configuration that supports distal portions of the fingers and the thumb of the user in a curled position (a semi-closed "fist") when the palmar grip 52 is grasped in the palm of the user. The palmar grip 52 can be fabricated, using any conventional technique such as molding, from any rigid or semi-rigid material such as high density polyethylene. The palmar grip 52 includes first and second channels 52C1, 52C2 (see FIG. 8) formed through the length thereof (in a side-by-side orientation).

One end of the grip strap 56 is affixed to the surface of the proximal support shell 22 adjacent the cusp formed by the integral thumb extension 22T protruding from the proximal support shell 22 by any conventional means, e.g., a rivet 56R as illustrated in FIG. 4. The free end of the grip strap 56 is inserted through the first channel 52C1 of the palmar grip 52, passed through the affixed retaining ring 54, and inserted through the second channel 52C2 of the palmar grip 52 so that the free end of the grip strap 56 passes over the affixed end of the grip strap 56.

Once the palmar grip 52 is integrated in combination with the grip strap 56 as described in the preceding paragraph, the palmar grip 56 is approximately centered between the edges of the ulnar and radial surfaces of the proximal support shell 22 along a line extending between the cusp of the thumb extension 22T and the affixation point of the grip strap 56. That is, the palmar grip 52 of the described embodiment has a diagonal orientation with respect to the centerline of the proximal support shell 22 (see FIG. 3).

The ratchet assembly 58 comprises a ratchet buckle 58RB and a ratchet strap 58S. The ratchet buckle 58RB is affixed to the dorsal surface of the proximal support shell 22 in such manner that the ratchet buckle 58RB has a diagonal orientation with respect the centerline thereof, i.e., the orientation of the ratchet buckle 58RB is approximately parallel to that of the palmar grip 52 (this diagonal orientation facilitates the application of the tensioning force). The ratchet strap 58S, which is fabricated of a plastic or rubber material, includes a segment having a plurality of teeth configured for engagement with the ratchet buckle 58RB. One end thereof is affixed to the free end of the grip strap 56 by any conventional means, e.g., a rivet 58R as illustrated in FIG. 3. Activation of the ratchet buckle 58RB causes movement of the ratchet strap 58S, which exerts a tensioning force on the grip strap 56, and concomitantly the palmar grip 52, that causes the hand and wrist of the user to be firmly positioned against the inner surfaces of the protective shell assembly 20 (or the protective shell inner liner (or inner support layer 24L) if the forelimb brace device 10 is configured to include both inner support layers (or only the inner support layer 24L)) while concomitantly allowing the user to wrap his fingers, thumb, and hand around the palmar grip 52. This ensures that the user's lower limb maintains a skeletal orientation that is defined by the tensioned configuration of the forelimb brace device 10.

One skilled in the art will appreciate that other embodiments of an adjustable palmar-grip anchoring mechanism can be used firmly position the hand, wrist, and forearm of the user firmly against the inner surfaces of the protective shell assembly 20 (or the protective shell inner liner (or inner support layer 24L) if the forelimb brace device 10 is configured to include both inner support layers (or only the inner support layer 24L)). For example, the palmar grip can be formed with a single aperture (see reference numeral 52A in FIG. 6) through the center thereof for the grip strap, which would eliminate the need for the retaining ring. One end of the grip strap would be affixed to the proximal support shell 22 in the position where the retaining ring was affixed in the embodiment described above, with the free end of the grip strap passing through the single aperture of the palmar grip and affixed to the ratchet strap as described above. Sliding movement of the grip strap within the palmar grip would be easier in this embodiment due to reduced frictional forces acting on the grip strap.

Alternatively, the palmar grip could be formed without apertures and the grip strap would comprise two segments. One segment of the grip strap would have its ends affixed to the proximal support shell 24 as described in the preceding paragraph and one end of the palmar grip, respectively. The other segment of the grip strap would be affixed to the other end of the palmar grip and the ratchet strap, respectively.

Figure 9:
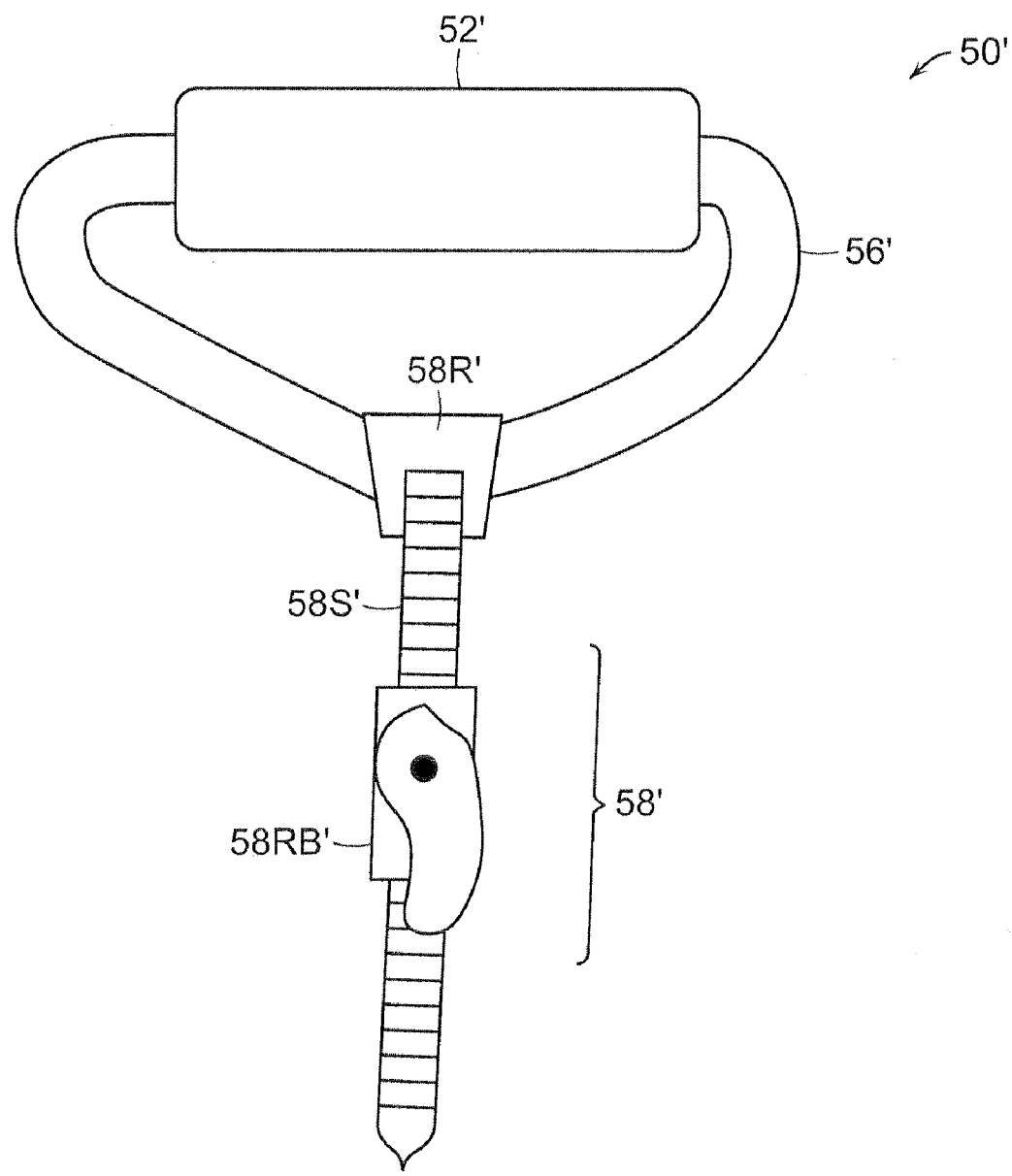
FIG. 9 is a plan view of a preferred embodiment of an adjustable palmar-grip anchoring mechanism for the forelimb brace device according to the present invention.

Another embodiment of the adjustable palmar-grip anchoring mechanism 50' is illustrated in FIGS. 9 and comprises a palmar grip 52', a guide ring (not illustrated), a grip strap 56', and a ratchet assembly 58'. The guide ring is positioned and affixed to the proximal support shell 22 as described above to facilitate positioning of the grip strap 56' (optionally, the guide ring may be omitted). The palmar grip 52' is formed with a single aperture for the grip strap 56'. The grip strap 56' is inserted through the aperture, with one end of the grip strap 56' passing through the guide ring 54' and the other end passing over the cusp formed by the integral thumb extension 22T protruding from the proximal support shell 22 so that the free ends of the grip strap 56' overlap at the centerline of the dorsal surface of the proximal support shell 22. The ratchet assembly 58' comprises a ratchet buckle 58RB' and a ratchet strap 58S'. The ratchet buckle 58RB' is affixed to the dorsal surface of the proximal support shell 22 in such manner that the ratchet buckle 58RB' is aligned along the centerline of the proximal support shell 22. The ratchet strap 58S' is engaged with the ratchet buckle 58RB' and one end thereof is affixed to the overlapped free ends of the grip strap 56' by any conventional means, e.g., a rivet 58R' as illustrated in FIG. 9. Activation of the ratchet buckle 58RB' causes a tensioning movement of the ratchet strap 58S', which exerts a tensioning force on the grip strap 56' that causes the hand and wrist of the user to be firmly positioned against the ventral surfaces of the protective shell assembly 20 (or the protective shell inner liner (or inner support layer 24L) if the forelimb brace device 10 is configured to include both inner support layers (or only the inner support layer 24L)).

Figure 2:
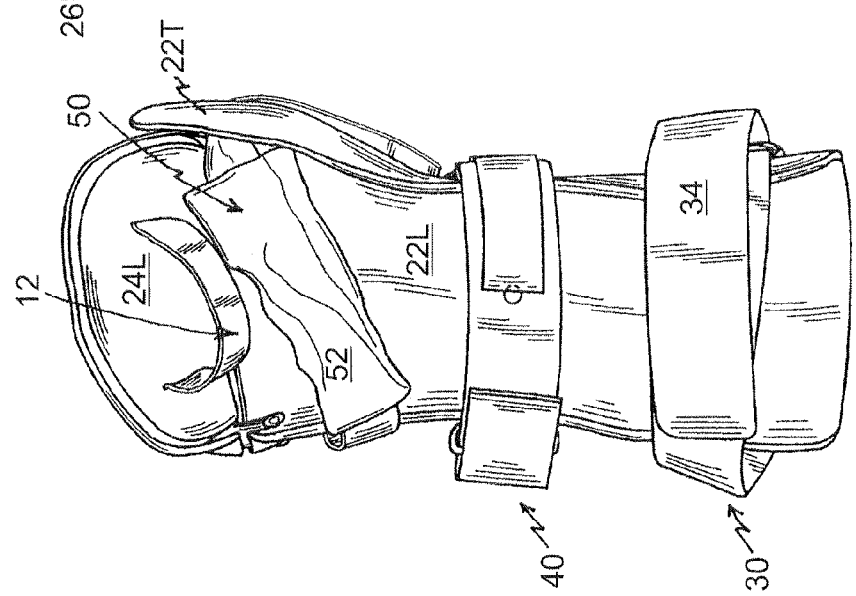
FIG. 2 is a palmar perspective view of a forelimb brace device constructed according to the teachings of the present invention, showing the proximal support shell, the thumb portion of the proximal support shell, the distal support shell, a finger anchor strap, the palmar arch grip, palmar grip anchor straps, wrist anchor members, forearm anchor members, strap elements, and metacarpophalangeal joint mechanisms of one embodiment of the invention.
Figure 7:
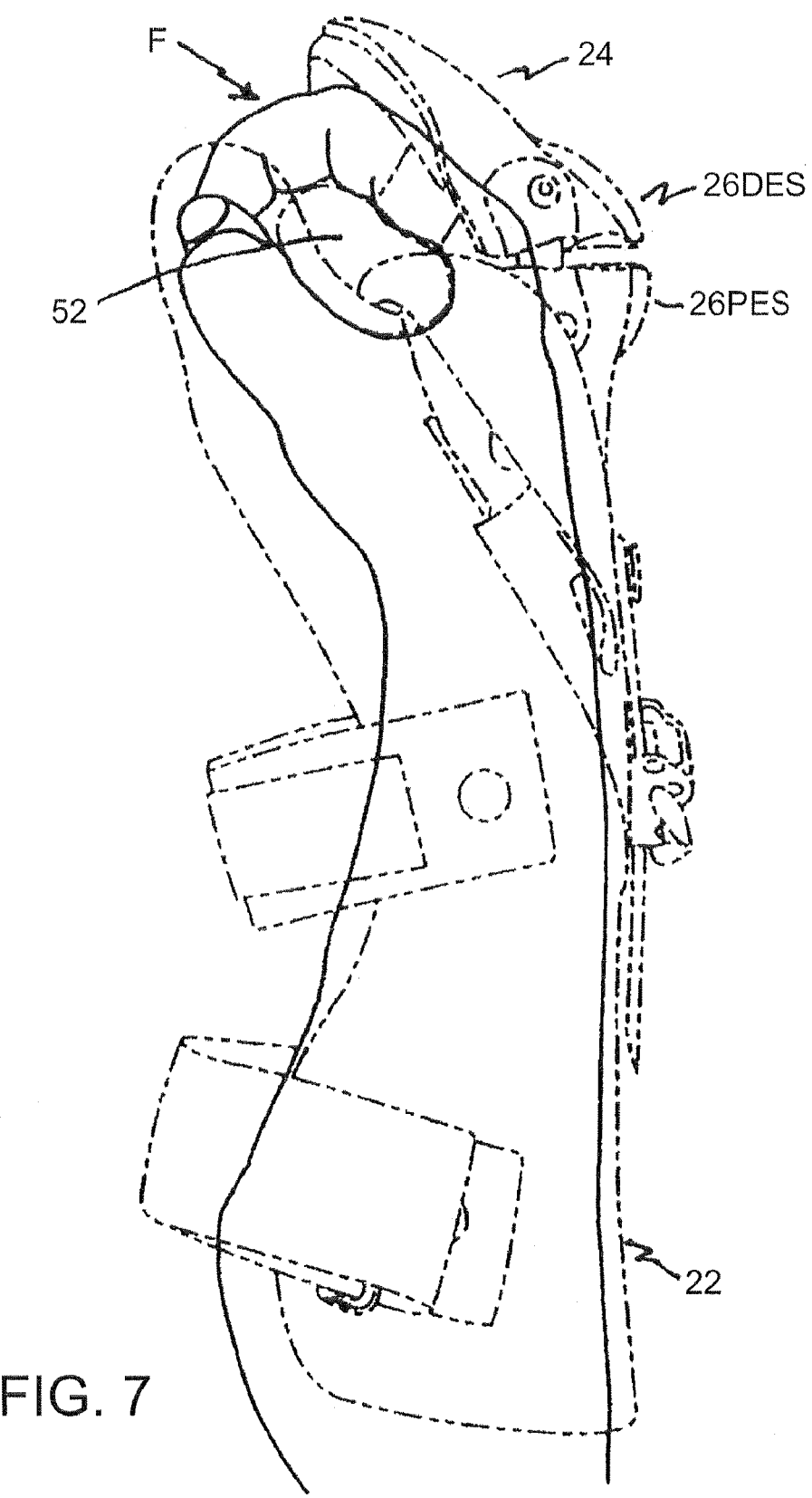
FIG. 7 is a phantom view of the forelimb brace device of FIG. 2 secured to a user's forelimb.
Figure 8:
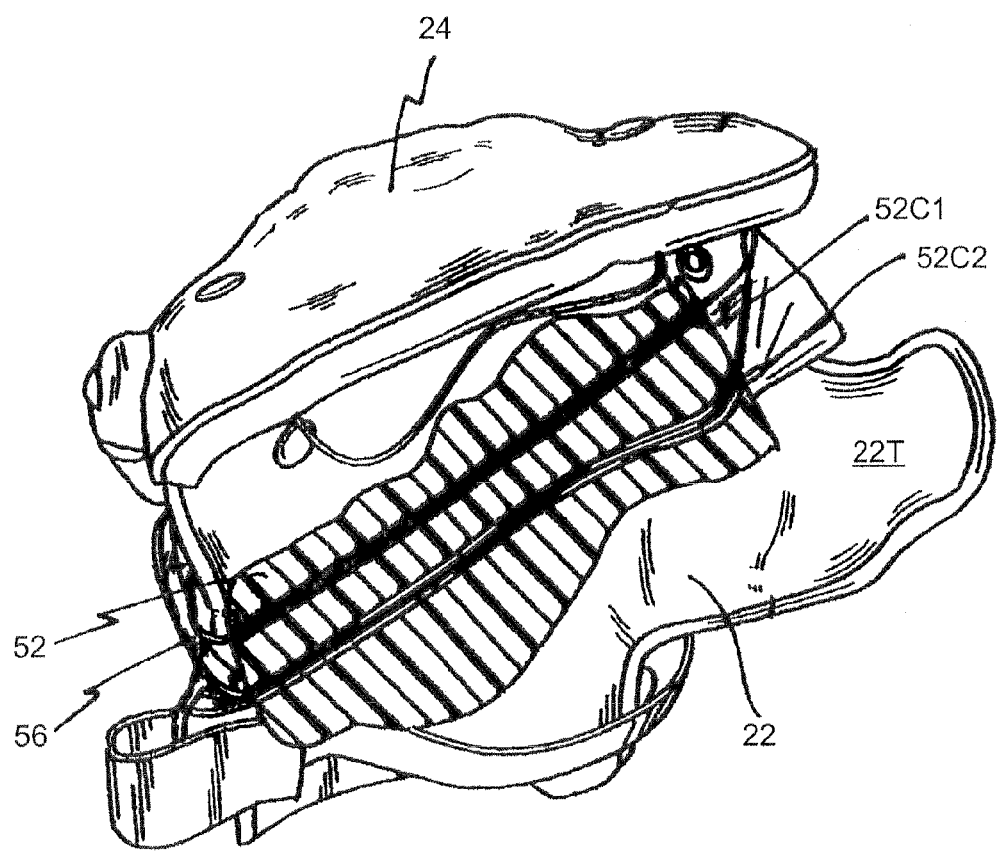
FIG. 8 is a cut-away, cross-sectional view of the forelimb brace device of FIG. 2 showing the palmar arch grip section with the proximal support shell and distal support shell.

Referring to FIGS. 2, 5 and 6, the finger retention strap 12 secures the user's fingers against the inner surface of the distal support shell 24 (or the inner support layer 24L if the forelimb brace device 10 is so configured). Finger retention strap 12 can be fabricated of any material suitable for withstanding abduction and other forces when forelimb brace device 10 is being used. The strap 12 is secured to the inner surface of the distal support shell 24 by any conventional fastening means, e.g., rivets 12R are illustrated in FIG. 3. If the forelimb brace device 10 includes the inner support layer 24L, corresponding apertures are formed in the inner support layer 24L so that the retention strap 12 passes therethrough (see FIG. 2).

A key feature of the forelimb brace device 10 according to the present invention is the cooperative interaction among the MCP joint assembly 26, the adjustable forearm anchoring mechanism 30, the adjustable wrist anchoring mechanism 40, the adjustable palmar-grip anchoring mechanism 50, and the finger retention strap 12 to position and secure the protective shell assembly 20 in combination with the fingers, hand, wrist, and forearm of a user. Such cooperative interaction immobilizes the wrist in a predetermined flexion position or adduction angle, depending upon the tensioning forces applied, to prevent injuries to the user's wrist. The predetermined wrist flexion position or adduction angle provided by the interacting structural and functional elements of the forelimb brace assembly 10 according to the present invention is within the range from a neutral wrist flexion position or adduction angle (hand approximately parallel to the forearm) to a 3° wrist flexion position or adduction angle (hand rotated upwardly approximately 3° with respect to the forearm).

The MCP joint subassembly 26 interactively cooperates with the proximal and distal support shells 22, 24, the finger retention strap 12, and the adjustable palmar-grip anchoring assembly 50 to maintain the user's fingers F around palmar grip 52, thereby positioning the proximal phalanges of the fingers F at a selected angle of flexion sufficient to prevent hyperextension and other injuries of the fingers F.

Moreover, in the embodiment shown in FIGS. 3-7, the MCP joint subassembly 26 is operative to provide an "extension stop" while the user's forelimb is in flexion. In particular, the proximal extension stop 26PES and the distal extension stop 26DES of the MCP joint subassembly 26 (see FIGS. 4, 6), when in abutting engagement, restrict movement of the user's phalanges within a safe, limited distance, thereby preventing hyperextension of the users fingers F, metacarpal section M, and wrist W. When extension stops 26PES, 26DES abuttingly engage as a result of a user's fall, distal support shell 24 and proximal support shell 22 absorb the impact energy due to such a fall and transmit this impact force throughout the structural elements comprising the forelimb brace device 10, instead of such impact force being directly transmitted to the user's forelimb. Further, the finger retention strap 12 secures the position of the user's fingers F to prevent sprains or fractures thereof during any such fall.

Additionally, the forelimb brace device 10 according to the present invention prevents hyperextension, Gamekeeper's Thumb and other injuries, by the placement of the user's thumb and hand within protective shell assembly 20 and finger retention strap 12 as well as around palmar grip 52.

The forelimb brace device 10 according to the present invention can be fitted, assembled and used in the following manner. First, the user passes his/her gloved or ungloved hand through forearm anchor strap 34, the wrist anchor strap 44, and beneath and around palmar arch grip 52, placing his/her fingers within finger retention strap 12. The user then selectively tightens forearm anchor strap 34 and wrist anchor strap 44 to draw the user's forelimb firmly against proximal support shell 22, including thumb extension 22T, and the distal support shell 24. The user then actuates the adjustable palmar-grip anchoring mechanism 50 to selectively tighten and draw the user's hand firmly against palmar grip 52 and the protective shell assembly 20.

A variety of modifications and variations of the present invention are possible in light of the above teachings. For example, in the described embodiments of the adjustable palmar-grip anchoring assembly the grip strap and the ratchet strap were described as separate and distinct elements. One skilled in the art will appreciate that the ratchet strap and the grip strap could be fabricated as an integrated component. Alternatively, the ratchet strap could be fabricated as a unitary configuration that eliminates the need for the grip strap. Or, the ratchet strap could be fabricated as a unitary configuration that eliminates the need for the grip strap, and a cushioning pad integrated in combination with such a unitary ratchet strap wherein the cushioning pad is configured and positioned to abut against the user's forearm and/or wrist, as applicable. It is therefore to be understood that, within the scope of the appended claims, the present invention may be practiced other than as specifically described herein.

What is claimed is:

1. A forelimb brace device for protecting the fingers, hand, wrist, and forearm of a user from impact injuries, comprising:
   a proximal support shell;
   a distal support shell;
   a finger retention strap integrated in combination with said distal support shell;
   an MCP joint subassembly that interconnects said proximal support shell and said distal support shell to permit pivotal movement between said proximal support shell and said distal support shell;
   an adjustable forearm anchoring mechanism integrated in combination with said proximal support shell and adjustable in tension to secure said forelimb brace device against the forearm of the user;
   an adjustable wrist anchoring mechanism integrated in combination with said proximal support shell and adjustable in tension to secure said forelimb brace device against the wrist of the user; and an adjustable palmar-grip anchoring mechanism integrated in combination with said proximal support shell, said adjustable palmar-grip anchoring mechanism including a palmar grip for positioning the fingers and hand of the user, said adjustable palmar-grip anchoring mechanism being adjustable in tension to secure the hand and wrist in said forelimb brace device;

wherein interactive cooperation among said MCP joint subassembly, said adjustable forearm anchor mechanism, said adjustable wrist anchoring mechanism, and said adjustable palmar-grip anchoring mechanism immobilizes the wrist of the user in a predetermined flexion position.

2. The forelimb brace device of claim 1 wherein said adjustable wrist anchoring mechanism comprises:

a retaining ring affixed to one lateral surface of said proximal support shell; and a hook and loop fastener strap having one end thereof affixed to the other lateral surface of said proximal support surface;

wherein said hook and loop fastener strap is integrated in combination with said retaining ring such that the other end thereof can be manipulated by the user to apply tension to said hook and loop fastener strap to secure said forelimb brace device against the wrist of the user.

3. The forelimb brace device of claim 1 wherein said adjustable wrist anchoring mechanism comprises:

a buckle integrated in combination with one lateral surface of said proximal support shell; and a belt means affixed to the other lateral surface of said proximal support shell;

wherein said belt means and said buckle are integrated in combination by the user to apply tension to said belt means to secure said forelimb brace device against the wrist of the user.

4. A forelimb brace device for protecting the fingers, hands, wrist, and forearm of a user from impact injuries, comprising:

a proximal support shell;

a distal support shell;

an MCP joint subassembly that interconnects said proximal support shell and said distal support shell to permit pivotal movement between said proximal support shell and said distal support shell;

an adjustable forearm anchoring mechanism integrated in combination with said proximal support shell and adjustable in tension to secure said forelimb brace device against the forearm of the user;

an adjustable wrist anchoring mechanism integrated in combination with said proximal support shell and adjustable in tension to secure said forelimb brace device against the wrist of the user; and an adjustable palmar-grip anchoring mechanism integrated in combination with said proximal support shell, said adjustable palmar-grip anchoring mechanism including a palmar grip for positioning the fingers and hand of the user, said adjustable palmar-grip anchoring mechanism being adjustable in tension to secure the hand and wrist in said forelimb brace device; said adjustable palmar-grip mechanism comprising a strap means integrated in combination with said palmar grip and a ratchet assembly affixed to the dorsal surface of said proximal support shell in a specified orientation with respect to the centerline thereof and integrated in combination with said strap means for movement therebetween; said ratchet assembly being operative to cause movement of said strap means wherein tension is applied to said strap means and said palmar grip in combination therewith;

wherein interactive cooperation among said MCP joint subassembly, said adjustable forearm anchor mechanism, said adjustable wrist anchoring mechanism, and said adjustable palmar-grip anchoring mechanism immobilizes the wrist of the user in a predetermined flexion position.

5. The forelimb brace device of claim 4 wherein said strap means is integrated in combination with said proximal support shell by means of a retaining ring; and wherein the specified orientation of said affixed ratchet assembly is diagonal with respect to the centerline of said proximal support shell.

6. The forelimb brace device of claim 4 wherein the specified orientation of said affixed ratchet assembly is along the centerline of said proximal support shell.

7. A forelimb brace device for protecting the fingers, hand, wrist, and forearm of a user from impact injuries, comprising:

a proximal support shell;

a distal support shell;

an MCP joint subassembly that interconnects said proximal support shell and said distal support shell to permit pivotal movement between said proximal support shell and said distal support shell;

an adjustable forearm anchoring mechanism integrated in combination with said proximal support shell and adjustable in tension to secure said forelimb brace device against the forearm of the user; said adjustable forearm anchoring mechanism comprising a ratchet buckle integrated in combination with one lateral surface of said proximal support shell and a strap means having one end thereof affixed to the other lateral surface of said proximal support means and the other end thereof integrated in combination with said ratchet buckle; said ratchet buckle being operative to cause movement of said strap means wherein tension is applied to said strap means to secure said forelimb brace device against the forearm of the user;

an adjustable wrist anchoring mechanism integrated in combination with said proximal support shell and adjustable in tension to secure said forelimb brace device against the wrist of the user; and an adjustable palmar-grip anchoring mechanism integrated in combination with said proximal support shell, said adjustable palmar-grip anchoring mechanism including a palmar grip for positioning the fingers and hand of the user, said adjustable palmar-grip anchoring mechanism being adjustable in tension to secure the hand and wrist in said forelimb brace device;

wherein interactive cooperation among said MCP joint subassembly, said adjustable forearm anchor mechanism, said adjustable wrist anchoring mechanism, and said adjustable palmar-grip anchoring mechanism immobilizes the wrist of the user in a predetermined flexion position.

8. A forelimb brace device for protecting the fingers, hand, wrist, and forearm of a user from impact injuries, comprising:

a proximal support shell;

a distal support shell;

an MCP joint subassembly that interconnects said proximal support shell and said distal support shell to permit pivotal movement between said proximal support shell and said distal support shell;

an adjustable forearm anchoring mechanism integrated in combination with said proximal support shell and adjustable in tension to secure said forelimb brace device against the forearm of the user;

and an adjustable wrist anchoring mechanism integrated in combination with said proximal support shell and adjustable in tension to secure said forelimb brace device against the wrist of the user, said adjustable wrist anchoring mechanism comprising a ratchet buckle integrated in combination with one lateral surface of said proximal support shell and a strap means having one end thereof affixed to the other lateral surface of said proximal support means and the other end thereof integrated in combination with said ratchet buckle; said ratchet buckle being operative to cause movement of said strap means wherein tension is applied to said strap means to secure said forelimb brace device against the wrist of the user; and an adjustable palmar-grip anchoring mechanism integrated in combination with said proximal support shell, said adjustable palmar-grip anchoring mechanism including a palmar grip for positioning the fingers and hand of the user, said adjustable palmar-grip anchoring mechanism being adjustable in tension to secure the hand and wrist in said forelimb brace device;

wherein interactive cooperation among said MCP joint subassembly, said adjustable forearm anchor mechanism, said adjustable wrist anchoring mechanism, and said adjustable palmar-grip anchoring mechanism immobilizes the wrist of the user in a predetermined flexion position.

9. The forelimb brace device of claim 8 further comprising:

an inner support layer integrated in combination with the inner surface of said distal support shell.

10. The forelimb brace device as in claim 8 or 9 further comprising:

an inner support layer integrated in combination with the inner surface of said proximal support shell.

11. The forelimb brace device of claim 8 wherein said MCP joint subassembly further comprises:

a proximal stop structure associated with said proximal support shell; and a distal stop structure associated with said distal support shell;

wherein abutting engagement between said proximal stop structure and said distal stop structure limits the pivotal movement between said proximal support shell and said distal support shell.

12. The forelimb brace device of claim 8 wherein said adjustable forearm anchoring mechanism comprises:

a retaining ring affixed to one lateral surface of said proximal support shell; and a hook and loop fastener strap having one end thereof affixed to the other lateral surface of said proximal support surface;

wherein said hook and loop fastener strap is integrated in combination with said retaining ring such that the other end thereof can be manipulated by the user to apply tension to said hook and loop fastener strap to secure said forelimb brace device against the forearm of the user.

13. The forelimb brace device of claim 8 wherein said adjustable forearm anchoring mechanism comprises:

a buckle integrated in combination with one lateral surface of said proximal support shell; and a belt means affixed to the other lateral surface of said proximal support shell;

wherein said belt means and said buckle are integrated in combination by the user to apply tension to said belt means to secure said forelimb brace device against the forearm of the user.

14. The forelimb brace device of claim 8 wherein said MCP joint subassembly for interconnecting said proximal support shell and said distal support shell comprises:

spaced-apart proximal joint housings associated with said proximal support shell;

spaced-apart distal joint housings associated with said distal support shell, said spaced-apart distal joint housings corresponding in number and opposed relation to said spaced-apart proximal joint housings; and a resilient member integrated in combination with opposed ones of said spaced-apart proximal and distal joint housings;

wherein said resilient members facilitate pivotal movement between said proximal support shell and said distal support shell.

* * * * *